US011317865B2

(12) United States Patent
Bly et al.

(10) Patent No.: US 11,317,865 B2
(45) Date of Patent: *May 3, 2022

(54) WEARABLE PHYSIOLOGIC SENSING APPARATUS

(71) Applicant: Aclaris Medical, LLC, Falcon Heights, MN (US)

(72) Inventors: Mark Bly, Falcon Heights, MN (US); Andrew Radtke, Minneapolis, MN (US)

(73) Assignee: Aclaris Medical, LLC, Falcon Heights, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/928,697

(22) Filed: Jul. 14, 2020

(65) Prior Publication Data
US 2020/0345302 A1 Nov. 5, 2020

Related U.S. Application Data

(63) Continuation of application No. 15/276,169, filed on Sep. 26, 2016, now Pat. No. 10,779,765.
(Continued)

(51) Int. Cl.
*A61B 5/00* (2006.01)
*A61B 5/0205* (2006.01)
(Continued)

(52) U.S. Cl.
CPC ........ *A61B 5/6826* (2013.01); *A61B 5/02055* (2013.01); *A61B 5/6831* (2013.01); *A61B 5/0024* (2013.01); *A61B 5/029* (2013.01); *A61B 5/02108* (2013.01); *A61B 5/02405* (2013.01); *A61B 5/02438* (2013.01);
(Continued)

(58) Field of Classification Search
None
See application file for complete search history.

(56) References Cited

U.S. PATENT DOCUMENTS 3,841,316 A 10/1974 Meyer
4,380,240 A * 4/1983 Jobsis ................. A61B 5/0059
356/41

(Continued)

OTHER PUBLICATIONS

Fairooz et al.; Performance Evaluation of Complex Electrical Bio-impedance from V/I Four-electrode Measurements; International Journal of Medical, Health, Biomedical, Bioengineering and Pharmaceutical Engineering; vol. 5, No. 9, 2011, pp. 441-453 (Year: 2011).

*Primary Examiner* — Nathan J Jenness
*Assistant Examiner* — James Moss
(74) *Attorney, Agent, or Firm* — Gallium Law; Wesley Schwie, Esq.; Isabel Fox

(57) ABSTRACT

The disclosure includes a system for sensing physiologic data. The system can include a flexible configured to wrap around a finger of a user, a first electrode coupled to the flexible strap, and a second electrode coupled to the flexible strap. The system can also include a sensor housing comprising at least one sensor configured to detect physiologic data from the finger and a data receiving module communicatively coupled to the first electrode, the second electrode, and the at least one sensor. The data receiving module can be configured to receive physiologic data from the at least one sensor.

7 Claims, 11 Drawing Sheets

Related U.S. Application Data

(60) Provisional application No. 62/234,015, filed on Sep. 28, 2015.

(51) Int. Cl.
    *A61B 5/0531*     (2021.01)
    *A61B 5/024*     (2006.01)
    *A61B 5/021*     (2006.01)
    *A61B 5/08*     (2006.01)
    *A61B 5/145*     (2006.01)
    *A61B 5/029*     (2006.01)
    *A61B 5/11*     (2006.01)
    *A61B 5/25*     (2021.01)

(52) U.S. Cl.
    CPC .......... *A61B 5/0531* (2013.01); *A61B 5/0816* (2013.01); *A61B 5/1118* (2013.01); *A61B 5/14542* (2013.01); *A61B 5/25* (2021.01)

(56) References Cited

U.S. PATENT DOCUMENTS

| | | | |
|---|---|---|---|
| 4,425,921 A * | 1/1984 | Fujisaki | A61B 5/6831 600/503 |
| 4,450,843 A | 5/1984 | Barney | |
| 4,625,732 A | 12/1986 | Kasa | |
| 4,830,014 A * | 5/1989 | Goodman | A61B 5/02427 600/310 |
| 5,766,131 A * | 6/1998 | Kondo | A61B 5/02416 600/310 |
| 6,026,322 A | 2/2000 | Korenman | |
| 6,516,289 B2 | 2/2003 | David | |
| 6,526,315 B1 | 2/2003 | Inagawa | |
| 6,671,532 B1 * | 12/2003 | Fudge | A61B 5/14552 221/26 |
| 9,711,060 B1 * | 7/2017 | Lusted | G09B 23/28 |
| 10,779,765 B2 * | 9/2020 | Bly | A61B 5/6826 |
| 2002/0156381 A1 | 10/2002 | Kao | |
| 2003/0023145 A1 | 1/2003 | Lee | |
| 2003/0100840 A1 * | 5/2003 | Sugiura | A61B 5/6838 600/504 |
| 2007/0038048 A1 * | 2/2007 | Gerder | A61B 5/02055 600/323 |
| 2007/0123756 A1 * | 5/2007 | Kitajima | A61B 5/14552 600/300 |
| 2007/0299322 A1 | 12/2007 | Miyajima | |
| 2008/0081963 A1 | 4/2008 | Naghavi | |
| 2008/0171918 A1 | 7/2008 | Teller | |
| 2008/0183052 A1 | 7/2008 | Teller | |
| 2008/0208016 A1 | 8/2008 | Hughes | |
| 2008/0221404 A1 | 9/2008 | Tso | |
| 2009/0105558 A1 | 4/2009 | Riley-Doucet | |
| 2010/0113952 A1 | 5/2010 | Raguin | |
| 2010/0168531 A1 | 7/2010 | Shaltis | |
| 2010/0174250 A1 | 7/2010 | Hu | |
| 2010/0210924 A1 * | 8/2010 | Parthasarathy | A61B 5/02055 600/301 |
| 2010/0234701 A1 | 9/2010 | Cho | |
| 2010/0324388 A1 | 12/2010 | Moon | |
| 2013/0023775 A1 * | 1/2013 | Lamego | A61B 5/6826 600/479 |
| 2014/0107554 A1 | 4/2014 | Bushby | |
| 2014/0213037 A1 | 7/2014 | LiCausi | |
| 2014/0275845 A1 | 9/2014 | Eagon | |
| 2015/0201875 A1 * | 7/2015 | Tateda | A61B 5/72 600/324 |
| 2015/0305632 A1 * | 10/2015 | Najarian | A61B 5/7207 600/301 |
| 2016/0022210 A1 * | 1/2016 | Nuovo | A61B 5/318 600/301 |
| 2016/0066845 A1 | 3/2016 | Kwon | |
| 2016/0235325 A1 | 8/2016 | Chou | |
| 2017/0042478 A1 | 2/2017 | Zheng | |
| 2017/0124374 A1 | 5/2017 | Rowe | |
| 2017/0172519 A1 | 6/2017 | Stergiou | |
| 2017/0340209 A1 | 11/2017 | Klaassen | |
| 2018/0064356 A1 * | 3/2018 | Mendenhall | A61B 5/0205 |
| 2019/0008396 A1 * | 1/2019 | Baron | A61B 5/02438 |
| 2019/0029536 A1 * | 1/2019 | Moon | A61B 5/0245 |

* cited by examiner

WEARABLE PHYSIOLOGIC SENSING APPARATUS

STATEMENT REGARDING GOVERNMENT SPONSORED RESEARCH

This invention was made with government support under TR000346 awarded by the National Institutes of Health. The government has certain rights in the invention.

CROSS-REFERENCE TO RELATED APPLICATIONS

The entire contents of the following application are incorporated by reference herein: U.S. Non-provisional patent application Ser. No. 15/276,169; filed Sep. 26, 2016; and entitled WEARABLE PHYSIOLOGIC SENSING APPARATUS.

The entire contents of the following application are incorporated by reference herein: U.S. Provisional Patent Application No. 62/234,015; filed Sep. 28, 2015; and entitled WEARABLE PHYSIOLOGIC SENSING APPARATUS.

BACKGROUND

Field

The present disclosure relates to a wearable sensor for monitoring physiologic signals for the treatment of medical and mental health disorders.

Description of Related Art

Typical devices for the measurement of physiologic parameters from the fingers require the placement of sensors on separate fingers, resulting in the transmission of physiologic signals from distinct fingers. Existing platforms for the sensing of physiologic signals may orient a temperature sensor on a pad of one finger, a pulse sensor, or possibly a pulse oximeter on a pad of a second finger, and additional impedance or conductance sensors on pads of third and fourth fingers. This can result in the reduced use of the hand dedicated to obtaining the physiologic measurements, and limits the scope of the devices to clinical settings, or minimally for applications where a user will not require the use of the hand dedicated to obtaining the physiologic signals. This may remove the user from situations and environments where the full use of one or both hands are required.

Furthermore, the application of multiple sensors to multiple fingers is time consuming, increases the chance for errors to be made (e.g. sensor not connected or positioned incorrectly), and can reduce user compliance with monitoring. Accordingly, there is a need for systems and methods to remedy the deficiencies as described above.

SUMMARY

In some embodiments, a system for sensing physiologic data comprises a flexible strap elongate along a first direction, the flexible strap configured to wrap around a finger of a user; a first electrode coupled to the flexible strap, the first electrode comprising a first electrical conductor configured to conductively couple to the finger; a second electrode coupled to the flexible strap and spaced from the first electrode along the first direction, the second electrode comprising a second electrical conductor configured to conductively couple to the finger; a sensor housing comprising at least one sensor configured to detect physiologic data from the finger; and a data receiving module communicatively coupled to the first electrode, the second electrode, and the at least one sensor. The data receiving module can be configured to receive physiologic data from the at least one sensor.

The at least one sensor can comprise at least one of a thermistor, a photo detector, a pulse sensor, a photoplethysmography sensor, and a heat-flux sensor. As well, the first electrode and the second electrode can define an electrodermal activity sensor.

In some embodiments, the finger defines a palmar surface that faces the same direction as a palm of a hand of the user. When the system is coupled to the finger of the user, the first and second electrodes may not cover a central axis of the palmar surface of the finger.

Additionally, in some embodiments, when the system is coupled to the finger of the user at least 50% of an area of the first and second electrodes contacts a lateral skin surface of the finger. In some embodiments, when the system is coupled to the finger of the user at least 75% of the area of the first and second electrodes contacts the lateral skin surface of the finger.

The flexible strap may be stretchable with a modulus of elasticity between 0.05 and 1 lb/in of strap width. The flexible strap material may also be breathable, and have a moisture vapor transmission rate of at least 300 grams/$m^2$/24 hrs.

In some embodiments, the system comprises a cable that communicatively couples the data receiving module with the first electrode, the second electrode, and the at least one sensor. The data receiving module may comprise at least one of a smartphone, tablet, and smart watch. Additionally, the data receiving module may comprise a network interface connected for wirelessly communicating data to another device.

Even still, in some embodiments, the system may comprise a first female snap coupled to the flexible strap and conductively coupled to the first electrode. The system may also comprise a second female snap coupled to the flexible strap and conductively coupled to the second electrode.

In some embodiments, the first female snap is coupled to the first electrode via a first conductive portion that extends from a first side portion of the flexible strap away from the first electrode along at least the second direction that is perpendicular to the first direction. The first conductive portion can additionally extend away from the first electrode along the first direction. As well, in some embodiments, the second female snap is coupled to the second electrode via a second conductive portion that extends from a second side portion of the flexible strap away from the second electrode along at least the second direction. The second conductive portion can additionally extend away from the second electrode along the second direction.

Some embodiments of the system may further comprise a first male snap coupled to the sensor housing, wherein the first male snap is arranged and configured to snapably couple to the first female snap. Systems may also comprise a second male snap coupled to the sensor housing, wherein the second male snap is arranged and configured to snapably couple to the second female snap.

When the sensor housing is coupled to the flexible strap the first female snap may fold toward a middle portion of the flexible strap to thereby snapably receive the first male snap and the second female snap may fold toward the middle portion of the flexible strap to thereby snapably receive the second male snap. Additionally, when the sensor housing is coupled to the flexible strap the sensor housing may extend along a third direction that is perpendicular to the first direction and the second direction.

In some embodiments, the sensor housing comprises a thermistor, a photo detector, and a light emitting diode all disposed along a first surface of the sensor housing, and the first male snap and the second male snap are disposed along a second surface of the sensor housing that faces opposite the first surface. As well, in some embodiments, when the flexible strap is wrapped around the finger of the user and the sensor housing is coupled to the flexible strap, the thermistor, photo detector, and light emitting diode all face a skin surface of the finger.

Some embodiments of the system may comprise a third electrode coupled to the flexible strap and communicatively coupled to the data receiving module. The third electrode may be spaced from the first electrode along either the first direction or the second direction. As well, the third electrode may comprise a third electrical conductor configured to conductively couple to the finger. The system may even comprise a fourth electrode coupled to the flexible strap and communicatively coupled to the data receiving module. The fourth electrode may be spaced from the third electrode along the first direction. Additionally, the fourth electrode may be spaced from the second electrode along either the first direction or the second direction. The fourth electrode may comprise a fourth electrical conductor configured to conductively couple to the finger.

The disclosure also includes a system for sensing physiologic data that comprises a flexible strap elongate along a first direction, the flexible strap configured to wrap around a finger of a user; a first electrode coupled to the flexible strap, the first electrode comprising a first electrical conductor configured to conductively couple to the finger; a second electrode coupled to the flexible strap and spaced from the first electrode along either the first direction or a second direction that is perpendicular to the first direction, the second electrode comprising a second electrical conductor configured to conductively couple to the finger; a third electrode coupled to the flexible strap and spaced from the first and second electrodes along the first direction, the third electrode comprising a third electrical conductor configured to conductively couple to the finger; a fourth electrode coupled to the flexible strap, spaced from the first and second electrodes along the first direction, and spaced from the third electrode along either the first direction or the second direction, the fourth electrode comprising a fourth electrical conductor configured to conductively couple to the finger; a sensor housing comprising at least one sensor configured to detect physiologic data from the finger; and a data receiving module communicatively coupled to the first electrode, the second electrode, the third electrode, the fourth electrode, and the at least one sensor. The data receiving module may be configured to receive physiologic data from the at least one sensor.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments. The above and other features of the present invention will become more apparent by describing in detail exemplary embodiments thereof with reference to the accompanying drawings, in which.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Introduction

Figure 6:
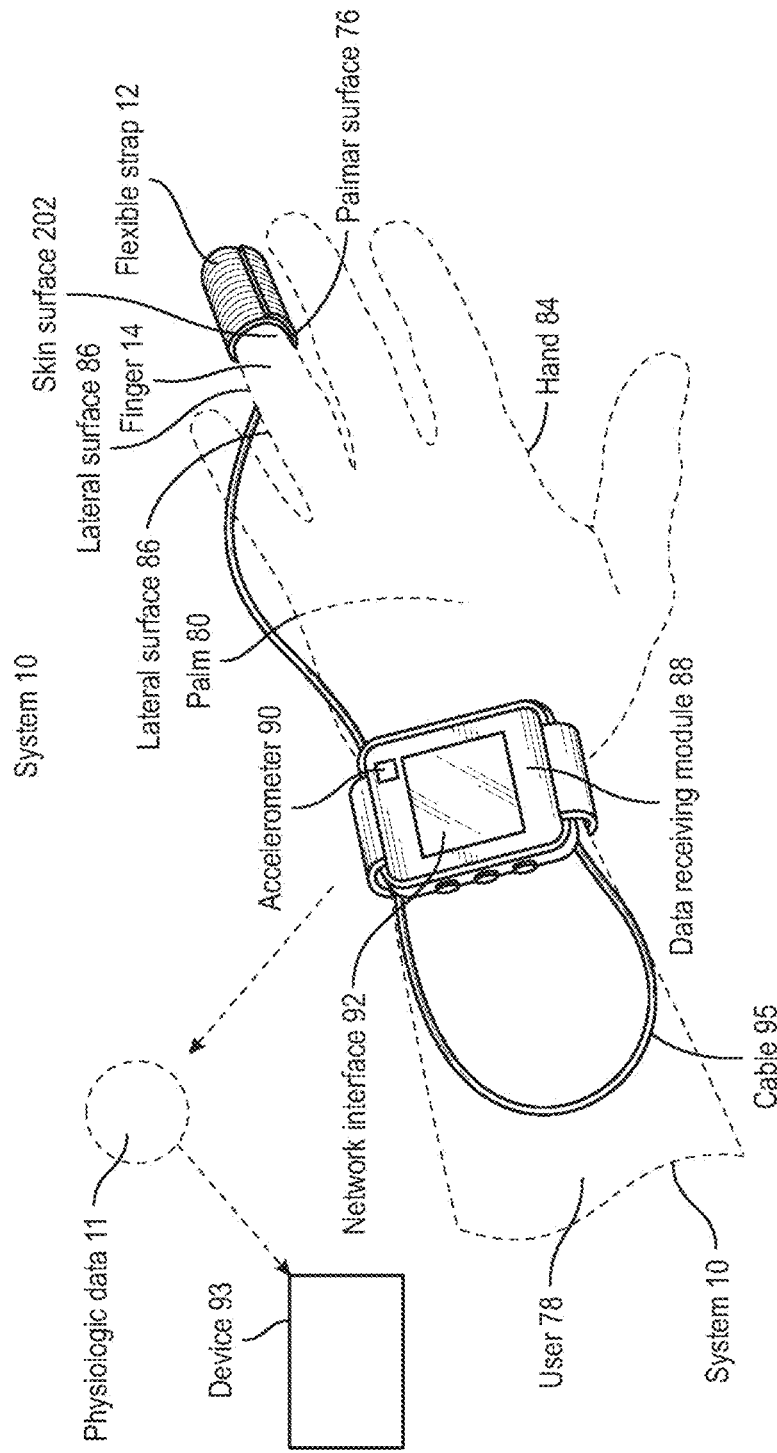
FIG. 6 is a perspective view of system and illustrates how the system can be configured to wrap around the finger of the user to collect and transmit physiological data of the user, according to some embodiments.

The physiologic signal-detecting system 10 can consist of at least 2 electrodes and at least one additional physiologic sensor located on a common finger 14. The system 10 can comprise a flexible strap 12, a first electrode 16, a second electrode 20, a sensor 26, a sensor housing 24, and a data receiving module 88. FIG. 6 illustrates a perspective view of a system 10 for sensing the physiological data 11 of a user 78. In some embodiments, the system 10 can comprise a flexible strap 12 elongate along a first direction X. The flexible strap 12 can be configured to wrap around a finger 14 of a user 78.

Figure 4:
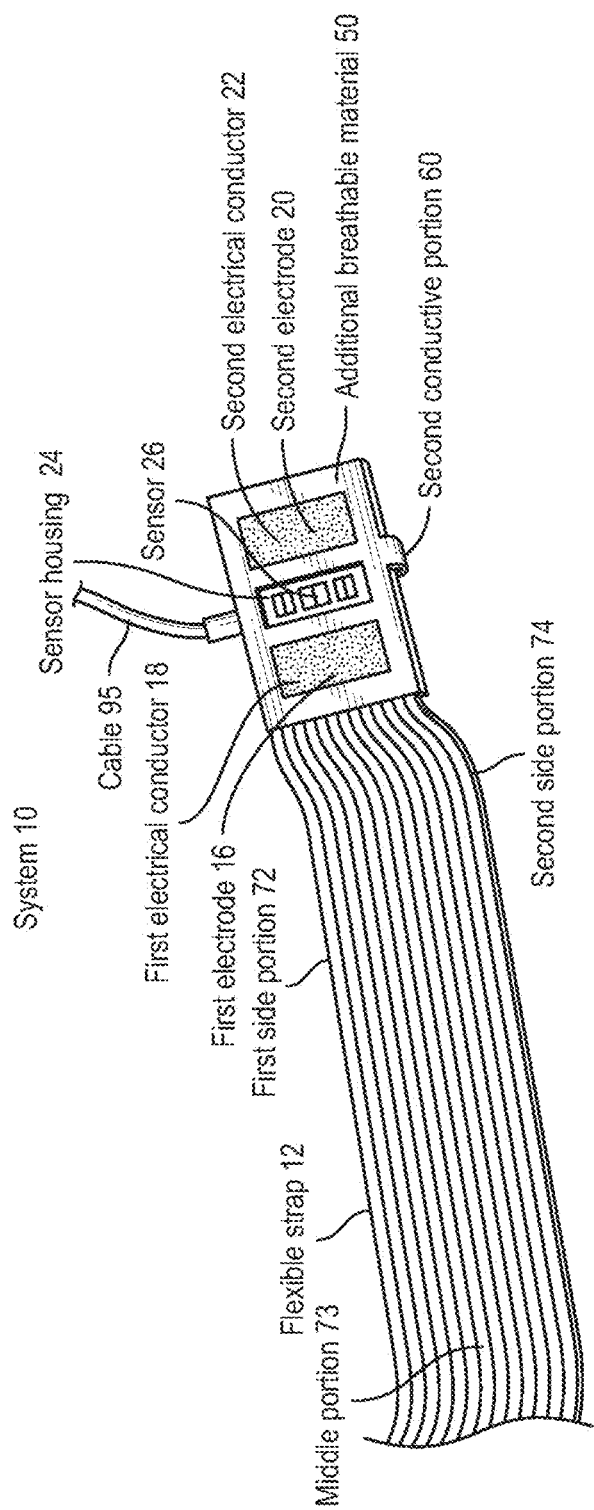
FIG. 4 illustrates the top view of the flexible strap, electrodes, and sensor housing, where the sensor housing is coupled to the flexible strap, according to some embodiments.

Referring to FIG. 4, the system 10 can also comprise a first electrode 16 that can be coupled to the flexible strap 12. The first electrode 16 can comprise a first electrical conductor 18 that can be configured to conductively couple to the finger 14 (shown in FIG. 6). The system 10 can include a second electrode 20 that can be coupled to the flexible strap 12 and can be spaced from the first electrode 16 along the first direction X. The second electrode 20 can comprise a second electrical conductor 22 that can be configured to conductively couple to the finger 14. The system 10 can also include a sensor housing 24. The sensor housing 24 can comprise at least one sensor 26 that can be configured to detect physiologic data 11 from the finger 14 (shown in FIG. 6). Additionally, the system can include a data receiving module 88 (shown in FIGS. 6 and 8) that can be communicatively coupled to the first electrode, second electrode, and at least one sensor 26. The data receiving module 88 can be configured to receive physiologic data 11 from at least one sensor 26.

Figure 8:
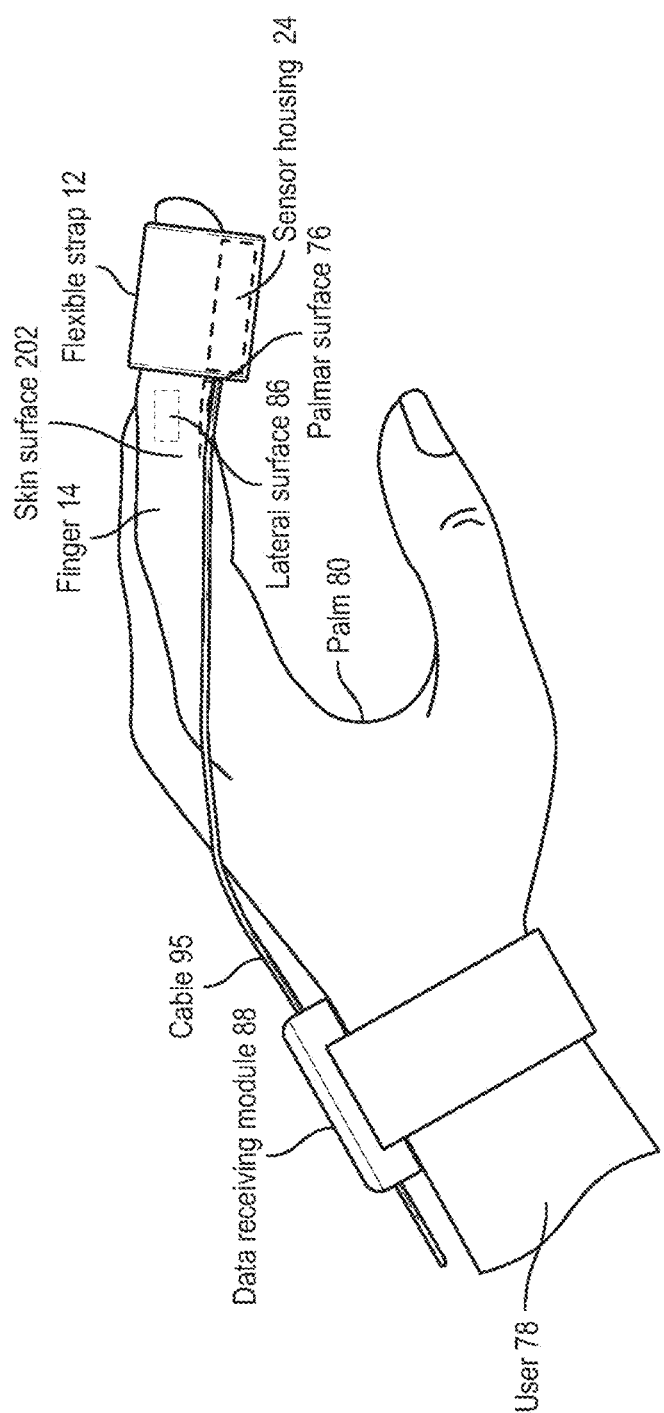
FIG. 8 illustrates a side view of the system configured to wrap around the finger of the user, according to some embodiments.

As illustrated in FIGS. 6 and 8, in several embodiments of the system 10, the finger 14 can define a palmar surface 76 that faces the same direction as a palm 80 of a hand 84 of the user 78. In some embodiments the first electrode 16 and second electrode 20 (shown in FIGS. 1 and 4) may not necessarily cover a central axis of the palmar surface 76 of the finger 14. The first electrode 16 and second electrode 20 may not necessarily pass through the central axis of the palmar surface 76 of the finger 14. Instead, the first electrode 16 and second electrode 20 may be positioned on the lateral surfaces 86 of the finger 14 and may extend circumferentially around the finger 14. The first electrode 16 and second electrode 20 may begin at, or near, (e.g. within 5 mm of) at least one additional physiologic sensor located on the palmar surface 76 of the finger 14 (e.g. on the finger pad). The lateral surfaces 86 can be the sides of the finger 14 that are exposed when the finger 14 is clamped between two flat surfaces. In other words, the lateral sides can be substantially perpendicular to the palmar surface 76 of the finger 14, where the fingerprint is located.

In some embodiments, wherein the system 10 can be coupled to the finger 14 of the user 78, at least 50% of the area of the first electrode 16 and second electrodes 20 can contact a lateral surface 86 of the finger 14. Additionally, in several embodiments, wherein the system 10 can be coupled to the finger 14 of the user 78, at least 75% of the area of the first electrode 16 and second electrode 20 can contact a lateral surface 86 of the finger 14.

Figure 1:
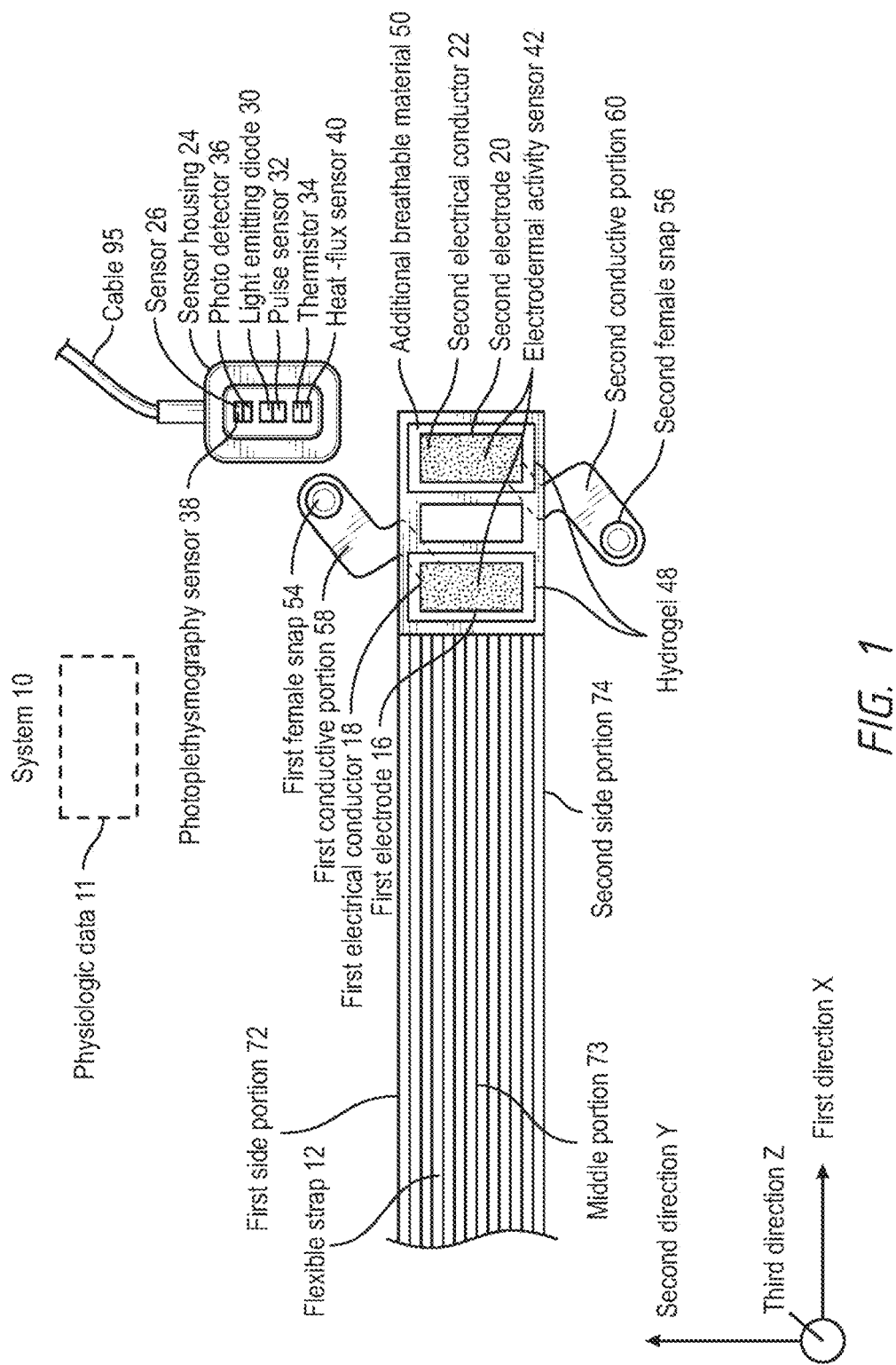
FIG. 1 illustrates a top view, or view that directly contacts the palmer surface of the finger, of the flexible strap, electrodes, and sensor housing, according to some embodiments.

Furthermore, the sensor 26 may be located on a common finger 14 segment. Referring to FIG. 1, in several embodiments of the system 10, at least one sensor 26 can comprise at least one of a thermistor 34, a photo detector 36, a pulse sensor 32, a photoplethysmography sensor 38, and a heat-flux sensor 40. Additional physiologic and movement characterization sensors may also be included with the sensor housing.

Electrodermal activity (EDA) refers to the conductance (or resistance, impedance, admittance) measurement made between electrodes positioned on the skin of the patient when a direct or alternating current is driven across the electrodes. The measurement is typically made on the fingers and/or hand, but can also be made on the dermal surface of the trunk and extremities (e.g. feet, wrists). Typically two electrodes are used, although multiple electrodes can be used as described in US patent application US20150031964. Most of the measured conductance is due to the electrode-skin contact resistance and the resistance of the superficial skin layer (e.g. stratum corneum). As a result, increases in sweat in the sweat ducts and on the skin surface cause corresponding increases in the conductance of the skin. This is known as EDA.

The term EDA is used herein to include both a tonic component (level) and a phasic component (response). The tonic component includes electrodermal level (EDL), skin conductance level (SCL), skin impedance level, skin admittance level, etc. A phasic component or response includes skin conductance response (SCR), galvanic skin reflex, galvanic skin response (GSR), electrodermal response (EDR), skin impedance response, skin admittance response, psychogalvanic reflex (PGR), etc. In the case of an AC measurement, it also includes a capacitive portion (susceptance) and phase angle. Referring the FIG. 1, the electrodermal activity (EDA) sensor 42 can consist of a minimum of two electrodes located on each side of the pulse sensor 32.

Referring back to FIG. 1, the first electrode 16 and the second electrode 20 can comprise a first electrical conductor 18 and a second electrical conductor 22, respectively. The electrodes can be flexible, allowing the electrode surfaces to conform to the skin surface 202 of a finger 14. These conductors can be a thin metal film or tape, a polymer or adhesive impregnated with conductive material, or a coated fabric or film (e.g. conductive silver chloride ink printed on a polyester film). The first electrical conductor 18 and the second electrical conductor 22 can comprise at least one of silver, silver chloride, carbon, copper, gold, stainless steel, nickel, platinum, or any other electrically conductive material. The first electrode 16 and second electrode 20 may be coated with a hydrogel 48 to improve conductivity and interface consistency. The hydrogel 48 can help absorb excessive moisture and supply moisture as the finger 14 dries. Hydrogel can also fill small gaps between the finger 14 and first electrode 16 or second electrode 20, which may not perfectly conform to the surface of the finger 14.

The hydrogel 48 may be made of different materials including, but not limited to, polyethylene glycol, polyethylene oxide, polyacrylic acid, and polyvinyl alcohol. The hydrogel may contain additional salts (e.g. NaCl, KCl, NaBr, KBr, $CaCl_2$)) to further improve conductivity. The hydrogel 48 (e.g. a liquid gel) can be pre-coated during the manufacture of the product or can be added by the user 78, clinician, or anyone associated with the system. The hydrogel 48 may extend beyond the first electrical conductor 18 or second electrical conductor 22. The hydrogel 48 may also cover a larger surface area than the first electrical conductor 18 or second electrical conductor 22. The surface area of the first electrical conductor 18, or second electrical conductor 22, or the hydrogel 48 may include, but is not limited to, the range 10-500 $mm^2$ (e.g. 300 $mm^2$). The hydrogel 48 may be covered with a liner 52 at the time of manufacture to protect the hydrogel 48. The liner 52 is removed from the hydrogel 48 prior to application of the hydrogel 48 to the finger 14 and can be reapplied to the hydrogel 48 after the hydrogel 48 is removed from the finger 14.

The first electrode 16 and second electrode 18 can comprise a breathable material (e.g. silver-coated fabric electrodes). In some embodiments, the flexible strap 12 can comprise a breathable material. In some embodiments, an additional breathable material 50 positioned around the electrodes against the skin and/or on the non-skin-contacting surface of the electrodes may be included. The breathable material can allow moisture to evaporate. In some cases, the breathable material may be moisture wicking (e.g. polyester) to improve moisture removal from the skin. In some embodiments, the electrodes may include a hole (i.e. annulus shape) or several holes to allow moisture to evaporate from the electrodes. If moisture is not allowed to evaporate from the skin, it can accumulate between the electrodes and skin surface 202. This may result in the shorting of the electrodes, such as causing a more highly conductive EDA output that may be more representative of sweat pooling under and around the electrodes than of the activation of the sweat glands. The evaporative removal of moisture can also improve comfort for the wearer. The moisture vapor transmission rate of the breathable material includes, but is not limited to, a range of at least 300 $g/m^2/24$ hrs. (e.g. 1000 $g/m^2/24$ hrs).

Figure 9:
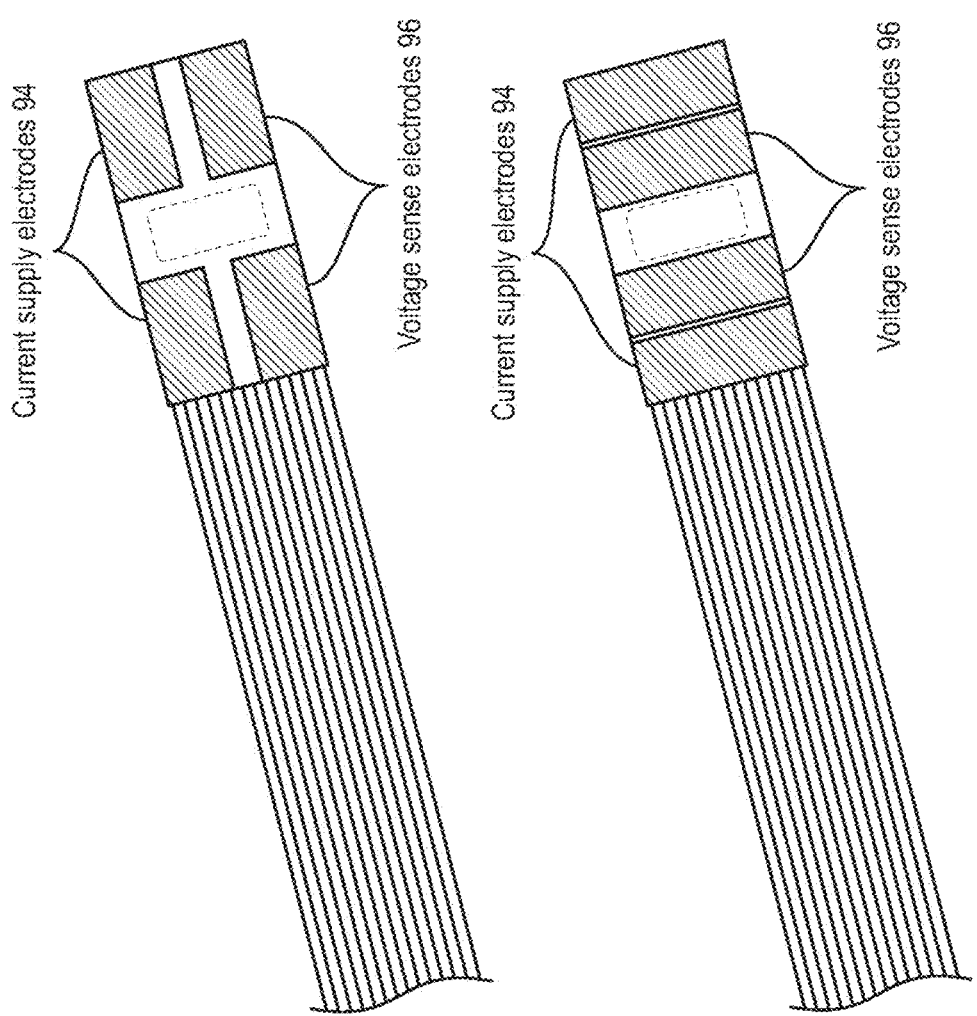
FIG. 9 illustrates a top view, or view that directly contacts the palmer surface of the finger, of the flexible strap, electrodes, and sensor housing, according to various embodiments.

Now, with reference to FIG. 9, instead of including electrodes to measure EDA, some embodiments of the system 10 can include at least four electrodes to make a 4-electrode bioimpedance measurement. With a 4-electrode measurement, current is supplied through two electrodes 94 (current supply electrodes 94), and voltage is measured from two separate electrodes 96 (voltage sense electrodes 96). This negates the effects of the electrode impedance and the impedance of a deeper underlying volume of tissue is measured instead of the skin and electrode surface impedance that dominate the two electrode measurement.

The four electrodes can enable measurement of the bioimpedance of the entire finger volume, which can indicate the overall amount of fluid in the finger. This could be used as an indicator of the amount of fluid in a limb resulting from conditions such as lymphedema or heart failure. These four electrodes could be positioned on a single finger segment or extend across multiple finger segments. Finally, the device could measure 4-electrode bioimpedance and EDA from the same four electrodes by switching between two circuits such that one or more 4-electrode bioimpedance measurements are taken from the electrodes with a 4-electrode bioimpedance measurement circuit and then at least two electrodes are switched to connect to a circuit for measuring EDA and one or more EDA measurements are made before switching back.

Referring back to FIG. 1, a pulse sensor 32, which can measure a blood volume pulse waveform, may be positioned against the finger 14 between the first electrode 16 and second electrode 20. The pulse sensor 32 can be a photoplethysmography (PPG) sensor 38 with at least one optical emitter (e.g. light emitting diode 30) and at least one photodetector 36 (e.g. photodiode, phototransistor). The light emitting diode 30 and photo detector 36 are likely oriented longitudinally on the palmar surface 76 of the finger 14 to maximize the space for the first electrode 16 and second electrode 20 of the electrode sensor. The light emitting diode 30 and photo detector 36 center-to-center spacing may include but not be limited to a range of 3 mm to 15 mm (e.g. 6 mm). The pulse sensor 32 could alternatively be another type of sensor than a PPG sensor (e.g. acoustic, 4-electrode bioimpedance).

Examples of the physiologic parameters which can be determined from the pulse signal, include heart rate (HR), heart rate variability (HRV), blood pressure (BP), pulse wave velocity (PWV), respiratory rate (RR), respiratory rate variability (RRV), tidal volume (VT), tidal volume variability (TVvar), minute ventilation (MV), stroke volume (SV), cardiac output (CO), cardiac index (CI), oxygen saturation (SPO2), and $CO_2$ concentration. Multiple sensors may be needed to determine some of the physiologic parameters. For example, two pulse sensors, or an ECG and pulse sensor, may be needed for measuring PWV.

A thermistor 34 or thermal sensor measuring temperature (e.g. thermocouple, diode temperature sensor, transistor temperature sensor) and/or a heat flux sensor 40 (e.g. Peltier module) may be positioned against the finger 14 between the first electrode 16 and second electrode 20 of the electrode sensor. The thermistor 34, or thermal sensor, may be included, in addition to, or instead of, the PPG sensor. The thermal sensor measures the changes in skin temperature and/or heat flux associated with vasoconstriction and vasodilation.

The sensors can be held to the finger 14 with a flexible strap 12 that wraps around the finger 14. The flexible strap 12 can be a linear strap that is wrapped around the finger 14 in one direction or two directions. Alternatively, the flexible strap 12 can be a loop that is stretched to fit over the finger 14. The flexible strap 12 can be made of a variety of material constructions including, but not limited to, knit, woven, non-woven, spun laced, foam, or thin polymer film. The flexible strap 12 material could be made of a variety of different materials including, but not limited to, polyester, rayon, polyurethane, silicone, polyethylene, polyvinyl chloride, and polyolefin. The flexible strap 12 can have an adhesive on the skin-facing side to stick to the finger or to itself. The flexible strap 12 material can also be designed to attach to itself without adhesive, or attached by a clip or other mechanism.

The flexible strap 12 may be stretchable with a low modulus of elasticity. The modulus of elasticity of the strap includes, but is not limited to, a range of 0.05-2 lb/inch of strap width or more narrowly 0.05-1 lb/inch. A flexible strap 12 with low modulus of elasticity is robust to variation in application tightness such that the pressure between the finger 14 and the PPG sensor varies only slightly with relatively larger variations in band tightness. Low application repeatability and reproducibility is expected by users 78; even so, other known systems do not incorporate a low modulus strap. Pulse oximetry monitors held to the finger 14 by relatively stiff tape have the tendency to be applied either too loosely or too tightly such that there is either poor contact or displacement of capillary blood under the sensor leading to poor signal quality. The flexible strap 12 may be integral to the sensor housing 24 (shown in FIG. 1) or detachable from the sensor housing 24 so that it can be replaced. The first electrode 16 and second electrode 20 (shown in FIG. 1) may be integrated into the flexible strap 12.

Figure 7:
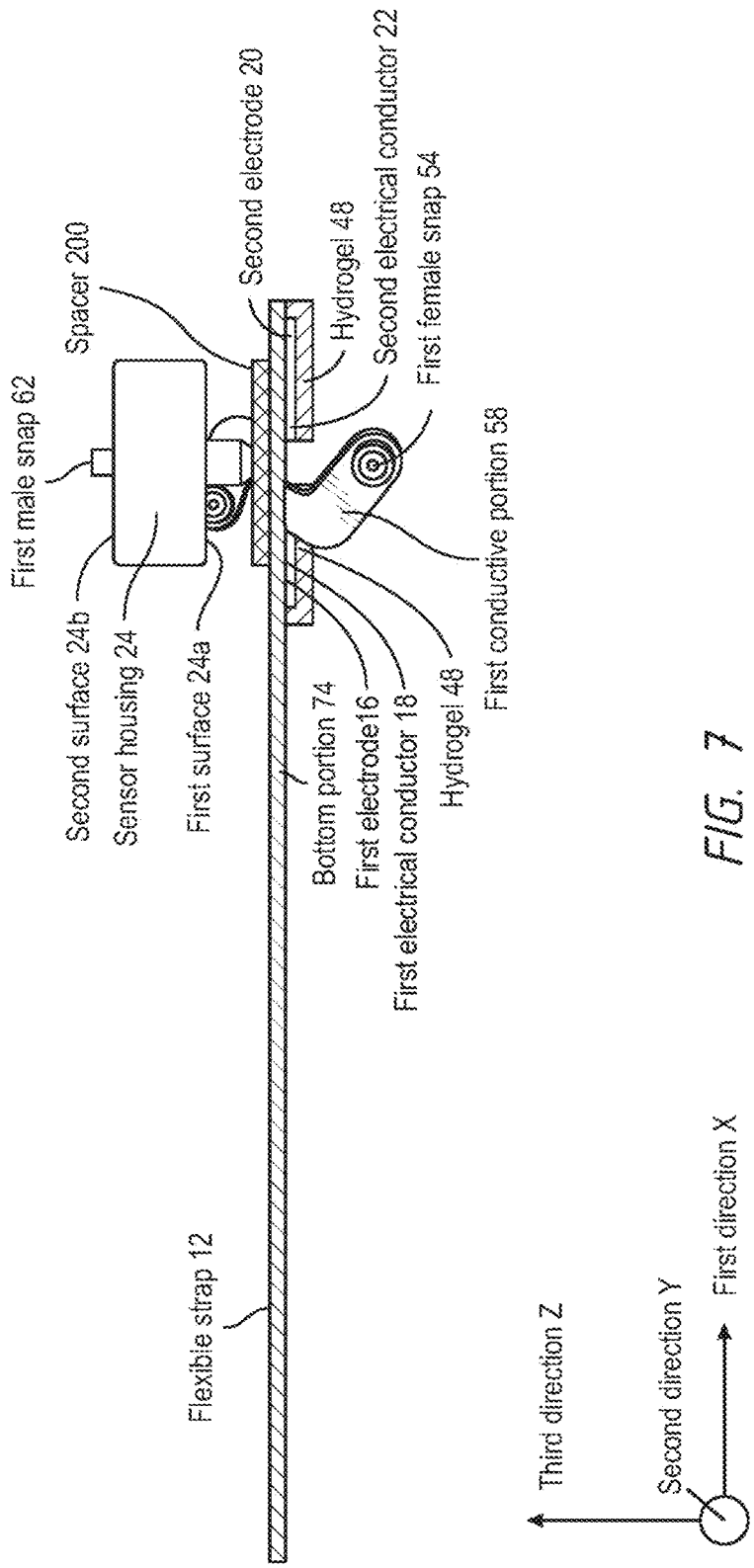
FIG. 7 illustrates a side view of the flexible strap, electrodes, and sensor housing, according to some embodiments.

FIGS. 1-4 illustrate how the sensor housing 24 can be coupled to the flexible strap 12 through the use of snaps. Referring to FIG. 1, the system 10 can comprise a first female snap 54 that can be coupled to the flexible strap 12 and can be conductively coupled to the first electrode 16. The system 10 can also comprise a second female snap 56. The second female snap 56 can be coupled to the flexible strap 12 and can be conductively coupled to the second electrode 20. In several embodiments, the first female snap 54 can be coupled to the first electrode 16 via a first conductive portion 58, shown in FIG. 1 and FIG. 2. The first conductive portion 58 can extend from a first side portion 72 away from the first electrode 16 along at least the second direction Y that can be perpendicular to the first direction X. The first conductive portion 58 can additionally extend away from the first electrode 16 along the first direction X. The second female snap 56 can be coupled to the second electrode 20 via a second conductive portion 60. The second conductive portion 60 can extend from a second side portion 74 away from the second electrode 20 along at least the second direction Y that can be perpendicular to the first direction X. The second conductive portion 60 can additionally extend away from the second electrode 20 along the first direction X. Furthermore, as shown in FIG. 7, the sensor housing 24 can extend along a third direction Z that can be perpendicular to the first direction X and the second direction Y.

Figure 3:
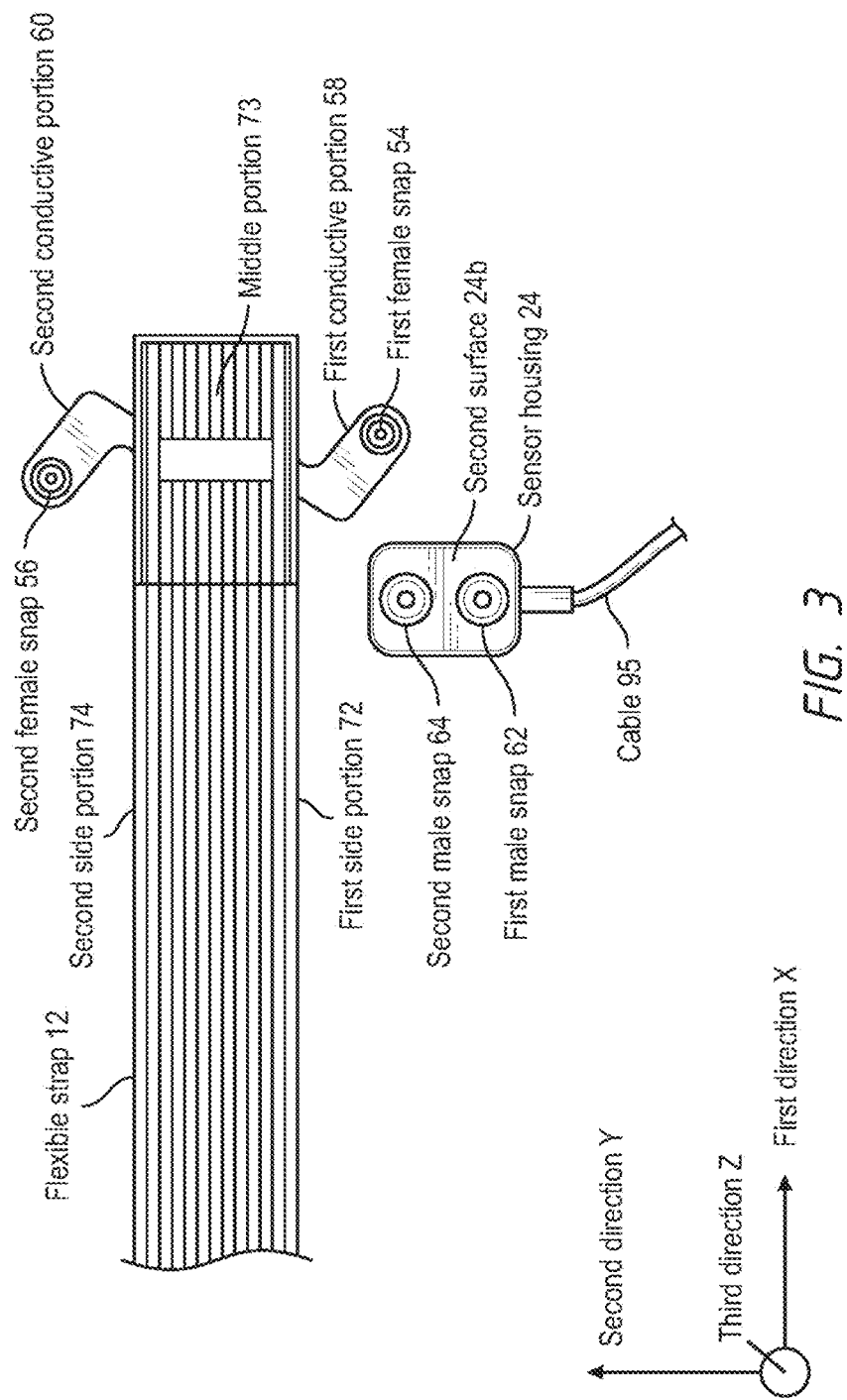
FIG. 3 illustrates a bottom view of the flexible strap and sensor housing, according to some embodiments.

In some embodiments, the system 10 can further comprise a first male snap 62 that can be coupled to the sensor housing 24. FIG. 3 illustrates the first and second male snaps 62, 64 on the sensor housing 24. The first male snap 62 can be arranged and configured to snapably couple to the first female snap 54. A second male snap 64 can be coupled to the sensor housing 24. The second male snap 64 can be arranged and configured to snapably couple to the second female snap 56.

Figure 5:
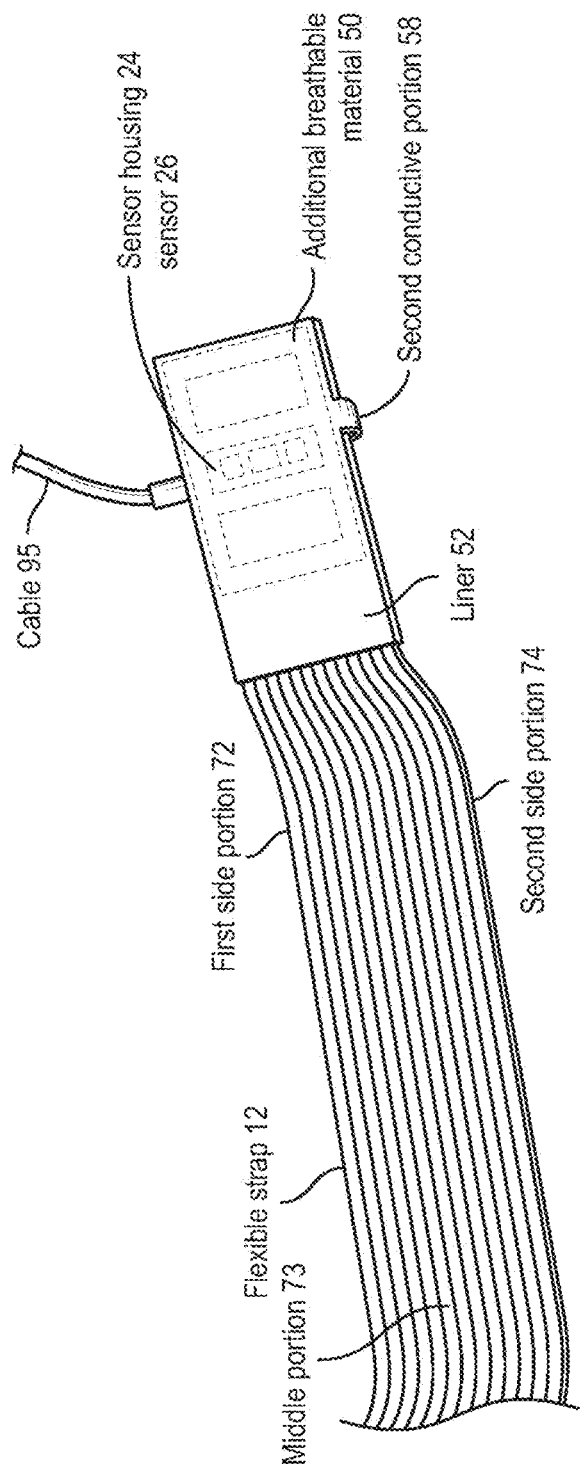
FIG. 5 illustrates the top view of the system, where the sensor is coupled to the flexible strap, according to some embodiments.

In several embodiments, the sensor housing 24 can then be coupled to the flexible strap 12. The first female snap 54 can fold toward a middle portion 73 of the flexible strap 12 and can snapably receive the first male snap 62. The second female snap 56 can fold toward the middle portion 73 of the flexible strap 12 and can snapably receive the second male snap 64. FIGS. 4 and 5 show how the second conductive portion 60 can fold to allow the second female snap 56 and the second male snap 64 to snapably couple and connect the sensor housing 24 to the flexible strap 12. FIG. 7 illustrates how to couple the sensor housing to the flexible strap 12 by folding the first conductive portion 58 with the first female snap 54 toward the sensor housing. The first female snap 54 can then snapably couple to the first male snap 62.

Figure 2:
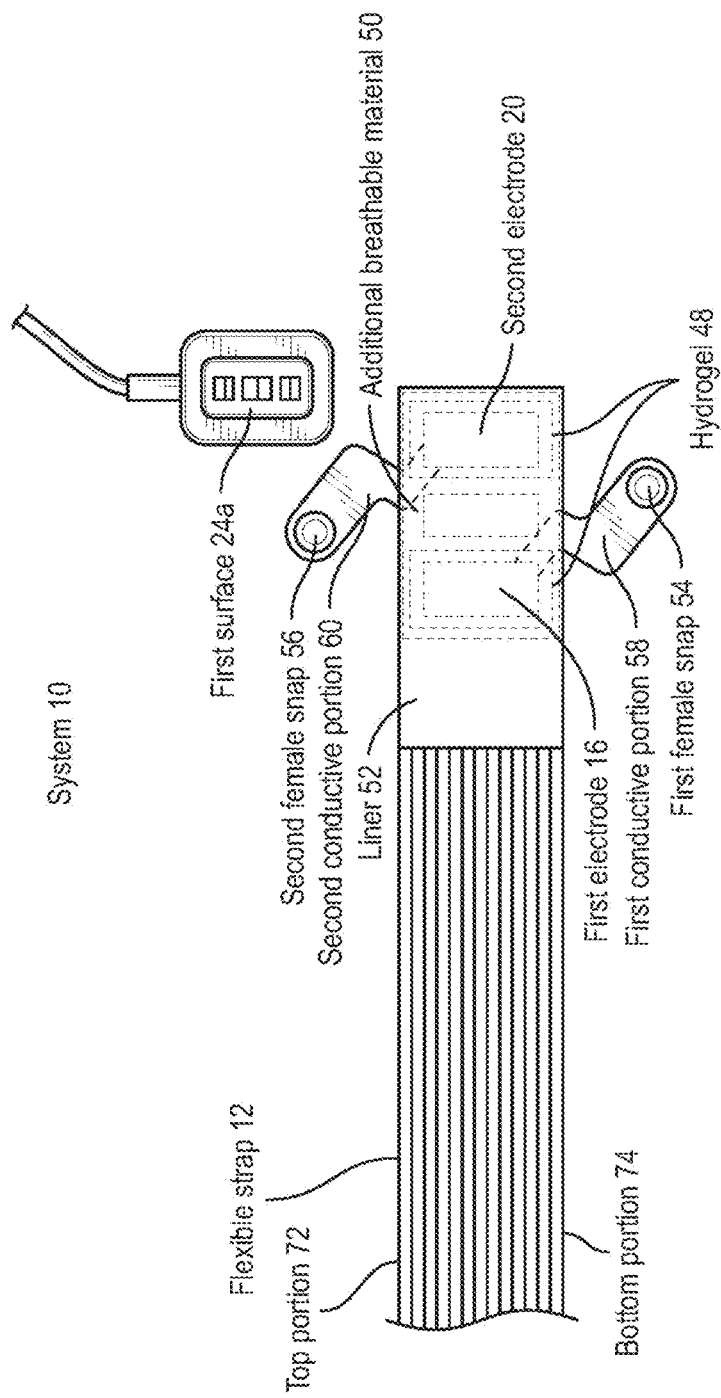
FIG. 2 illustrates a top view of the flexible strap and electrodes with hydrogel and protective liner and a top view of the sensor housing, according to some embodiments.

The electrical circuit including a processor and power source may be housed in the sensor housing 24, housed in a separate electronics housing of a data receiving module 88 (e.g. one that is mounted to the wrist) or distributed within multiple housings. As illustrated in FIG. 6, in some embodiments, the system 10 can further comprise a cable 95 that can communicatively couple the first electrode 16, the second electrode 20, and at least one sensor 26 with the data receiving module 88. FIGS. 1, 2, and 4 demonstrate how the cable 95 can attach to the sensor housing 24.

The electronics housing of a data receiving module 88 may be connected to the sensor housing 24 by a cable 95. The cable 95 can attach to the proximal side of a wrist-mounted electronics housing of the data receiving module 88. The cable 95 can include an adjustable loop so that the system 10 can be used on a wide range of different hand 84 sizes. While FIG. 6 shows the data receiving module 88 around the wrist of the user 78, in some embodiments, the data receiving module 88 can comprise at least one of a smartphone, tablet, and smart watch. In several embodiments, the data receiving module 88 can comprise a network interface 92 that can be connected for wirelessly communicating data 11 to another device 93.

Referring to FIG. 6, in several embodiments of the system 10, the data receiving module 88 can comprise an accelerometer 90. An accelerometer 90 may be included in the sensor housing 24, electronics housing of the data receiving module 88, or both. The accelerometer 90 measures accelerations at or near the location of the finger 14 or wrist and can be used in measuring motion and/or position. The accelerometer 90 signal can be used to determine whether the user 78 is active. This activity data can be useful as a clinical parameter (e.g. how much is the patient sleeping or walking in a day), as contextual information to interpret other data collected (e.g. the patient was sleeping or walking while the measurements were taken), or as a way of disregarding measurements (e.g. the patient was too active and so the data should not be trusted during this time).

At least one button may be included on the surface of the sensor housing 24 or electronics housing of the data receiving module 88. The button(s) may be used as marker buttons such that a timestamp is stored in memory when the marker button is pressed to indicate the time of an event. Alternatively, the button(s) may be used to initiate recording of a data stream.

The physiologic signal detecting device, or data receiving module 88, may output converted physiologic data 11. Data 11 may include one or more of the following: analog or digitized signals (e.g. EDA signal, pulse waveform, temperature), calculated parameters (e.g. HR, HRV, EDL, EDR rate [EDRs/min]). The physiological data 11 may be filtered, smoothed, averaged, counted, subtracted, added, mathematically combined, or processed with any known signal processing methods. The physiological data 11 or parameters may be further combined (e.g. HR and EDR rate or HRV, HR, and EDL) with an algorithm to create a useful output (e.g. index, status, prediction). The data may be used to provide a useful indication (e.g. autonomic nervous system activity, stress, distress, panic, physiologic reactivity to traumatic stimuli, arousal, hyperarousal, engagement, excitement, fear, sympathetic tone, parasympathetic tone, probability of dropout from therapy, fluid status, probability of hospitalization, probability of treatment success, probability of recovery). The physiological data 11 may be used to assist patients, therapists, and medical providers to diagnose, assign subtype, treat, monitor, reinforce progress, and motivate behavior.

Aclaris Medical, LLC has demonstrated that EDA can be reliably recorded with the physiologic signal-detecting device having a first electrode 16 and second electrode 20, positioned substantially on the lateral surfaces 86 of a single finger 14 segment, wrapping from the sensors 26 on the palmar finger surface 76 to the lateral surfaces 86 of the finger 14. The EDL measured from the Aclaris Medical device on the single finger 14 segment strongly correlates to the EDL measured with a BIOPAC Systems, Inc. data acquisition system from multiple fingers as is typically done. In another study, the EDL obtained from an Aclaris device with electrodes located on the ventral surface of the wrist was significantly lower and less strongly correlated with the BIOPAC EDL than the EDL obtained from same-finger electrodes. Representative traces can be seen in the figure below. The wrist electrodes commonly resulted in inconsistent responsiveness of the subjects to stressful stimuli within and across subjects.

Figure 10:
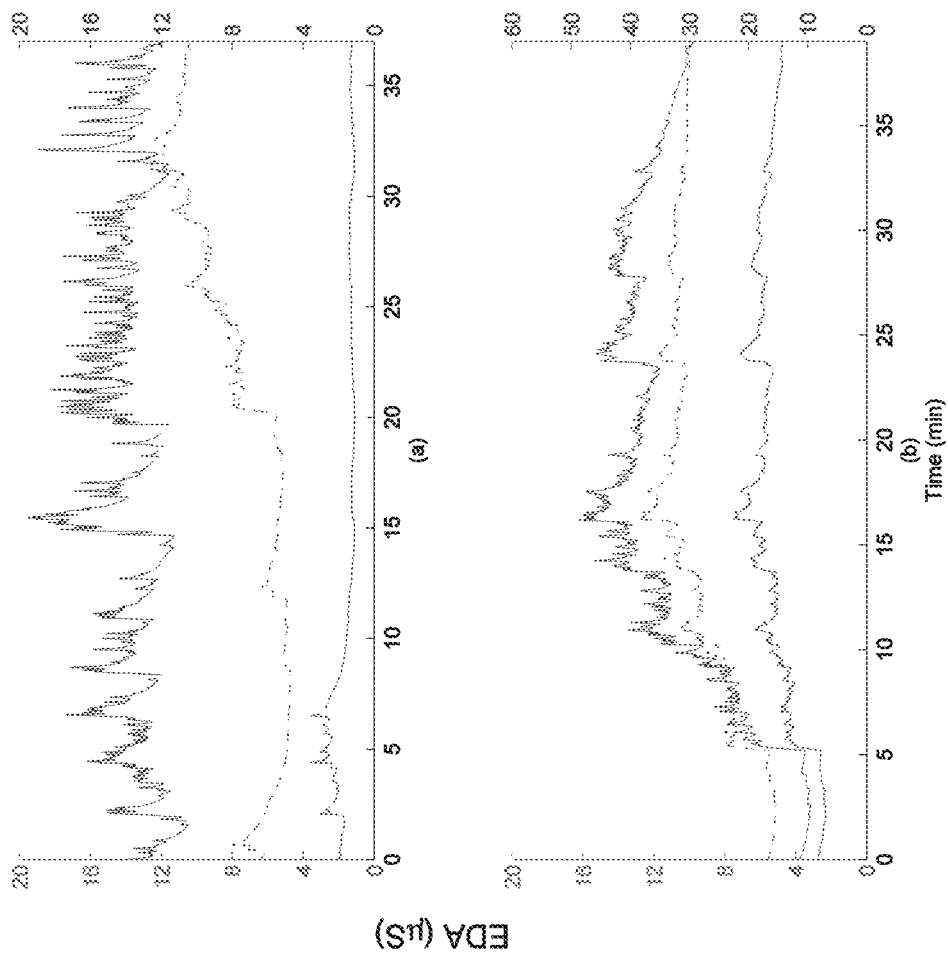
FIG. 10 illustrates typical EDA waveforms during cognitive and emotional stressors, according to some embodiments.

Typical EDA waveforms during cognitive and emotional stressors are shown in FIG. 10. The top traces in each plot are measurements from the BIOPAC electrodes located on (a) the hyopthenar eminences and (b) the thumb and little finger. The bottom 2 traces in each plot depict the corresponding conductance levels from EDA electrodes (a: solid line—ipsilateral wrist; dashed line—contralateral wrist; b: solid line—ipsilateral index finger; dashed line—ipsilateral middle finger).

Correlations between the Aclaris and BIOPAC EDL were evaluated over the entire recording session, which included both physical and autonomic nervous system response tasks. The correlations of the EDLs from the wrist electrodes were widely distributed between subjects, with coefficients ranging from −0.8 to 0.8. Conversely, the correlation coefficients from trials with the same-finger electrodes were tightly centered on 0.94, ranging from 0.8 to 0.99.

Figure 11:
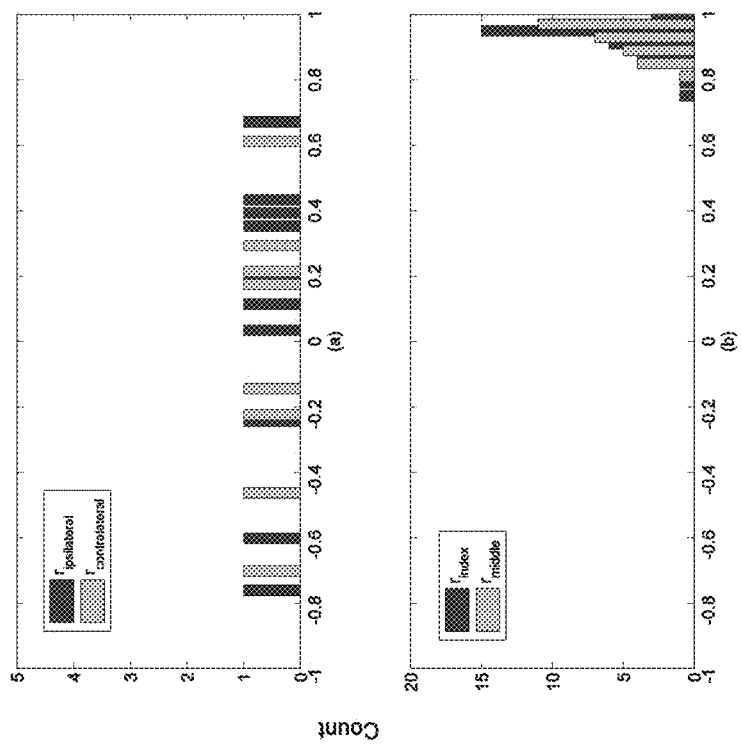
FIG. 11 illustrates distributions of correlation coefficients for the linear regressions of the BIOPAC and EDL measurements, according to some embodiments.

The distributions of correlation coefficients for the linear regressions of the BIOPAC and Aclaris EDL measurements taken from (a) the ipsilateral ($r_{ipsilateral}$, n=10) and contralateral wrists ($r_{contralateral}$, n=9) and (b) the index ($r_{index}$, n=30) and middle fingers ($r_{middle}$, n=28) are shown in FIG. 11.

Mean and standard deviations of trial durations and within-trial correlations between the Aclaris and Biopac EDL measurements are shown in the table below. (Abbreviations: i—ipsilateral to Biopac; c—contralateral to Biopac)

| Sensor Location | Trials, n | Duration (min) M | SD | r (Aclaris, Biopac) M | SD |
|---|---|---|---|---|---|
| Wrist, i | 10 | 85.3 | 4.3 | 0.06 | 0.46 |
| Wrist, c | 9 | 86.0 | 4.1 | −0.03 | 0.43 |
| Index | 30 | 119.7 | 7.8 | 0.92 | 0.05 |
| Middle | 28 | 102.6 | 37.2 | 0.93 | 0.04 |

In the same study, Aclaris also demonstrated that the positioning of the EDA electrodes to sides of the pulse sensor on the same finger segment still enables accurate heart rate measurement. In the table below, total trial heart rate deviation statistics and correlations between Biopac ECG and Aclaris finger PPG are displayed as the mean and (standard error) of the monitors' N trials. (Abbreviations: i—index; m—middle)

| Config | Trials, N | Mean deviation (bpm) | Mean absolute deviation (bpm) | Correlation coefficient |
|---|---|---|---|---|
| Finger, i | 30 | 0.18 (0.36) | 0.44 (0.39) | 0.96 (0.11) |
| Finger, m | 30 | 0.05 (0.18) | 0.35 (0.19) | 0.99 (0.03) |

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A system for sensing physiologic data, comprising:
   a flexible strap configured to surround at least a portion of a finger of a user;
   a first electrode located on the flexible strap and configured to contact the finger of the user;
   a second electrode located on the flexible strap and configured to contact the finger of the user, wherein at least one of the first electrode and the second electrode is configured to receive physiologic data from the finger of the user;
   at least one electrode snap assembly portion coupled to the flexible strap and conductively coupled to at least one of the first electrode and the second electrode; and
   a data receiving module communicatively coupled to at least one of the first electrode and the second electrode and coupled to at least one data receiving module snap assembly portion, the data receiving module configured to receive physiologic data from at least one of the first electrode and the second electrode,
   wherein the data receiving module is detachably coupled to the flexible strap,
   wherein the at least one electrode snap assembly portion comprises a first snap assembly portion and a second snap assembly portion, the first snap assembly portion coupled to the flexible strap that is elongate along a first direction and conductively coupled to the first electrode via a first conductive portion that extends from a first side portion of the flexible strap away from the first electrode along at least a second direction that is perpendicular to the first direction, the second snap assembly portion coupled to the flexible strap and conductively coupled to the second electrode via a second conductive portion that extends from a second side portion of the flexible strap away from the second electrode along at least the second direction, and
   wherein the at least one data receiving module snap assembly portion comprises a third snap assembly portion and a fourth snap assembly portion, wherein the third snap assembly portion is arranged and configured to snapably couple to the first snap assembly portion and wherein the fourth snap assembly portion is arranged and configured to snapably couple to the second snap assembly portion.

2. A flexible electrode strap, comprising:
   a flexible strap configured to surround at least a portion of a finger of a user;
   a first electrode directly coupled to the flexible strap and configured to contact the finger of the user, the first electrode conductively coupled to a first snap assembly portion;
   a second electrode directly coupled to the flexible strap and configured to contact the finger of the user, the second electrode conductively coupled to a second snap assembly portion; and
   at least one of the first electrode and the second electrode configured to receive physiologic data from the finger of the user.

3. The flexible electrode strap of claim 2, wherein the flexible strap is elongate along a first direction.

4. The flexible electrode strap of claim 3, the first snap assembly portion coupled to the flexible strap and conductively coupled to the first electrode via a first conductive portion that extends from a first side portion of the flexible strap away from the first electrode along at least a second direction that is perpendicular to the first direction, and the second snap assembly portion coupled to the flexible strap and conductively coupled to the second electrode via a second conductive portion that extends from a second side portion of the flexible strap away from the second electrode along at least the second direction,
   wherein the first snap assembly portion is arranged and configured to snapably couple to a third snap assembly portion coupled to a data receiving module, and
   wherein the second snap assembly portion is arranged and configured to snapably couple to a fourth snap assembly portion coupled to the data receiving module.

5. The flexible electrode strap of claim 2, wherein the second electrode is spaced from the first electrode along a first direction.

6. The flexible electrode strap of claim 2, wherein the first electrode and the second electrode are positioned on an inner surface of the flexible strap.

7. The flexible electrode strap of claim 2, further comprising an aperture extending through the flexible strap, the aperture configured to receive at least one sensor configured to detect physiologic data from the finger, wherein the aperture is located between the first electrode and the second electrode.

* * * * *